United States Patent
Pan et al.

(10) Patent No.: US 9,301,941 B2
(45) Date of Patent: Apr. 5, 2016

(54) METHODS FOR PREVENTING OR TREATING SARCOPENIA AND MUSCLE ATROPHY IN ANIMALS

(75) Inventors: Yuanlong Pan, Chesterfield, MO (US); Sunil Kochhar, Lausanne (CH); Serge Andre Dominique Rezzi, Lausanne (CH); Francois-Pierre Martin, Lausanne (CH); Emma Peré-Trepat, Lausanne (CH); Sebastiano Collino, Lausanne (CH); Francia Arce Vera, Lausanne (CH)

(73) Assignee: Nestec S. A, Vevey (CH)

( * ) Notice: Subject to any disclaimer, the term of this patent is extended or adjusted under 35 U.S.C. 154(b) by 127 days.

(21) Appl. No.: 13/499,118

(22) PCT Filed: Oct. 8, 2010

(86) PCT No.: PCT/US2010/002722
§ 371 (c)(1),
(2), (4) Date: Jun. 5, 2012

(87) PCT Pub. No.: WO2011/043827
PCT Pub. Date: Apr. 14, 2011

(65) Prior Publication Data
US 2012/0238515 A1    Sep. 20, 2012

Related U.S. Application Data

(60) Provisional application No. 61/278,633, filed on Oct. 9, 2009.

(51) Int. Cl.
| A61K 31/352 | (2006.01) |
| A23K 1/16 | (2006.01) |
| A23K 1/18 | (2006.01) |
| A61K 31/35 | (2006.01) |
| A61K 31/353 | (2006.01) |
| A23L 1/30 | (2006.01) |
| A61K 31/7034 | (2006.01) |
| A61K 36/48 | (2006.01) |

(52) U.S. Cl.
CPC .............. *A61K 31/35* (2013.01); *A23K 1/1618* (2013.01); *A23K 1/1846* (2013.01); *A23L 1/3002* (2013.01); *A61K 31/352* (2013.01); *A61K 31/353* (2013.01); *A61K 31/7034* (2013.01); *A61K 36/48* (2013.01)

(58) Field of Classification Search
CPC .. A61K 31/352; A23K 1/1618; A23K 1/1846
See application file for complete search history.

(56) References Cited

U.S. PATENT DOCUMENTS

| 4,163,746 A | 8/1979 | Feuer et al. |
| 2003/0021858 A1 | 1/2003 | Bababunmi |
| 2003/0203057 A1 | 10/2003 | Okada et al. |
| 2005/0049424 A1* | 3/2005 | Kelly et al. .................. 549/234 |
| 2005/0256181 A1 | 11/2005 | Distefano |
| 2007/0185012 A1 | 8/2007 | Rajadhyaksha et al. |
| 2008/0076829 A1 | 3/2008 | Dalton et al. |

FOREIGN PATENT DOCUMENTS

| EP | 1329222 | 7/2003 |
| WO | 2005089567 | 9/2005 |
| WO | 2007134867 | 11/2007 |

OTHER PUBLICATIONS

Rosenberg, I.H., J. Nutr., 1997, 127, p. 990S-991S.*
Doherty, T.J., J. Appl. Physiol., 2003, 95, p. 1717-1727.*
Definition of prevent, Oxford English Dictionary, http://dictionary.oed.com/, accessed online Mar. 27, 2010, especially definition 9a. at p. 2.*
Wu et al., Metabolism, 2004, 53(7), p. 942-948.*
Hidaka et al., Phyother. Res., 2003, 17, p. 112-119.*
Aubertin-Leheudre et al., Eur. J. Clin. Nutr., 2007, 61, p. 1442-1444.*
Cave et al., J. Anim. Physiol. Anim. Nutr., 2007, 91, p. 400-410.*
Joannou et al., J. Steroid Biochem. Molec. Biol., 1995, 54(3/4), p. 167-184.*
Definition of precursor, Oxford English Dictionary, http://www.oed.com/, accessed online on Jul. 7, 2015.*
Frantz et al. (Intern. J. Appl. Res. Vet. Med., 2007, 5(2), p. 57-64.*
Roudebush et al., JAVMA, 2008, 232(11), p. 1646-1655.*
PCT International Search Report and Written Opinion PCT/US2010/02722 Dated Jan. 11, 2011.
Aubertin-Leheudre et al., Short Communication: Six months of isoflavone supplement increases fat-free mass in obese-sarcopenic postmenopausal women: a randomized double-blind controlled trial; European Journal of Clinical Nutrition (2007) 61, 1422-1444.

* cited by examiner

*Primary Examiner* — Jonathan S Lau
(74) *Attorney, Agent, or Firm* — Ronald A. Burchett; Julie M. Lappin

(57) ABSTRACT

The invention provides methods for one or more of preventing or treating sarcopenia and muscle atrophy in animals. The methods comprise administering isoflavones to the animals, preferably in amounts of from about 0.001 to about 10 g/kg/day.

21 Claims, 1 Drawing Sheet

METHODS FOR PREVENTING OR TREATING SARCOPENIA AND MUSCLE ATROPHY IN ANIMALS

CROSS REFERENCE TO RELATED APPLICATIONS

This application is a national stage application under 35 U.S.C. §371 of PCT/US2010/002722 filed Oct. 8, 2010, which claims priority to U.S. Provisional Application Ser. No. 61/278,633 filed Oct. 9, 2009, the disclosures of which are incorporated herein by this reference.

BACKGROUND OF THE INVENTION

1. Field of the Invention

The invention relates generally to methods for preventing or treating sarcopenia and muscle atrophy and particularly to methods for using isoflavones for preventing or treating sarcopenia and muscle atrophy in animals.

2. Description of Related Art

Isoflavones are naturally occurring chemical compounds found in plants such as beans and legumes, particularly soy. Although the mechanism of action is unclear, isoflavones mimic the effects of estrogen and modulate estrogen metabolism. As a result, isoflavones are known to reduce tumor cell proliferation, induce tumor cell apoptosis, regulate hormone balance, and reduce the risks of breast and prostate cancer, heart disease, osteoporosis, and several other diseases and conditions. However, isoflavones are not known for preventing or treating sarcopenia or muscle atrophy.

During aging, there is a gradual decrease in the ability to maintain skeletal muscle function and mass. The condition is known as "sarcopenia." The exact cause of sarcopenia is unknown, but may be due to a combination of the gradual failure of "satellite cells" that help to regenerate skeletal muscle fibers and a decrease in sensitivity to or the availability of critical secreted growth factors that are necessary to maintain muscle mass and ensure satellite cell survival. Methods for combating sarcopenia are known in the art. U.S. Pat. No. 7,442,706 disclose methods for treating sarcopenia with growth hormone secretagogues. U.S. Pat. No. 7,232,580 and U.S. Pat. No. 7,138,148 disclose the use of extracts of *Ginkgo biloba* for preparing a medicament for the treatment of sarcopenia.

Similarly, muscle atrophy is defined as a decrease in the mass of the muscle. Muscle atrophy can be a partial or complete wasting away of muscle. When a muscle atrophies, it becomes weaker and, since the ability to exert force is related to mass, loses its ability to effectively support body functions, e.g., motion. Muscle atrophy can be caused by many factors, e.g., diseases such as cancer, AIDS, congestive heart disease, chronic obstructive pulmonary disease, renal failure, and severe burns. Often these animals suffer from "cachexia" and have a poor prognosis for good health or survival. Methods for combating muscle atrophy are known in the art. US20070122821 discloses antisense compositions and methods for treating muscle atrophy. US20060003959 discloses methods and agents for maintaining muscle mass and for preventing muscle atrophy and related biomarkers.

Despite these known methods, problems attributable to sarcopenia and muscle atrophy persist. There is, therefore, a need for novel methods for combating sarcopenia and muscle atrophy in animals, particularly aging animals.

SUMMARY OF THE INVENTION

It is, therefore, an object of the invention to provide methods for preventing or treating sarcopenia.

It is another object of the invention to provide methods for preventing or treating muscle atrophy.

One or more of these or other objects are achieved by administering isoflavones to animals in amounts sufficient for preventing or treating sarcopenia or muscle atrophy in the animals. In general embodiments, the isoflavones are administered to the animals in amounts of from about 0.001 to about 10 grams per kilogram of body weight per day (g/kg/day) for as long as there is a need for preventing or treating sarcopenia and muscle atrophy.

Other and further objects, features, and advantages of the invention will be readily apparent to those skilled in the art.

DETAILED DESCRIPTION OF THE INVENTION

Definitions

Figure 1:
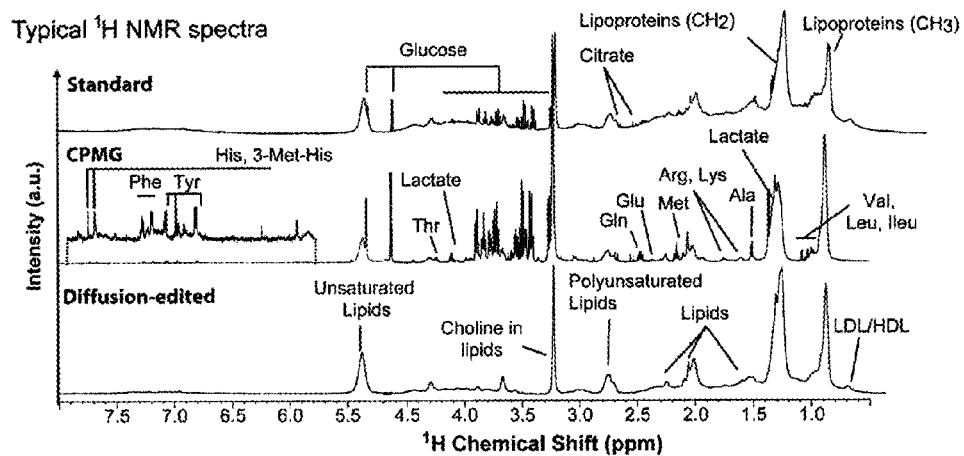
FIG. 1 illustrates metabolic profiles obtained from the metabolomic or metabonomic analysis of blood plasma using typical acquisition conditions (standard, CPMG, diffusion-edited spectra) on a 600 MHz nuclear magnetic resonance (NMR) spectrometer.

The term "isoflavones" means isoflavones and their natural or synthetic analogs, derivatives, precursors, and metabolites useful in the invention, including, but not limited to, isoflavones substituted with one or more lignans or coumestans, e.g., pinoresinol, lariciresinol, secoisolariciresinol, matairesinol, hydroxymatairesinol, syringaresinol, sesamin, enterodiol, enterolactone, and coumestrol.

The term "animal" means any animal susceptible to or suffering from sarcopenia or muscle atrophy, including human, avian, bovine, canine, equine, feline, hicrine, lupine, murine, ovine, or porcine animals.

The term "aging" means being of advanced age such that an animal is considered to be susceptible to sarcopenia.

The term "companion animal" means domesticated animals such as cats, dogs, rabbits, guinea pigs, ferrets, hamsters, mice, gerbils, horses, cows, goats, sheep, donkeys, pigs, and the like.

The term "dietary supplement" means a product that is intended to be ingested in addition to a normal animal diet. Dietary supplements may be in any form, e.g., solid, liquid, gel, tablet, capsule, powder, and the like. Preferably they are provided in convenient dosage forms, e.g., in sachets. Dietary supplements can be provided in bulk consumer packages such as bulk powders, liquids, gels, or oils. Similarly such supplements can be provided in bulk quantities to be included in other food items such as snacks, treats, supplement bars, beverages, and the like.

The term "regular basis" means that the isoflavones of the invention are administered to the animal on a regular and periodic basis over time. For example, the isoflavones can be administered monthly, weekly, or daily as appropriate for the animal. More frequent administration such as twice or three times daily is preferred in certain embodiments.

Ranges are used herein as shorthand to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "an animal", "a method", or "a disease" includes a plurality of such "animals", "methods", or "diseases." Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

The methods and compositions and other advances disclosed herein are not limited to particular methodologies, protocols, and reagents because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

The Invention

In one aspect, the invention provides methods for preventing or treating sarcopenia. The methods comprise administering to the animals a sarcopenia preventing or treating amount of one or more isoflavones. In another aspect, the invention provides methods for preventing or treating muscle atrophy. The methods comprise administering to the animals a muscle atrophy preventing or treating amount of one or more isoflavones. The inventions are based upon the discovery that isoflavones can be used to ameliorate changes in muscle caused by aging or caused by diseases or conditions that cause muscle atrophy.

In various embodiments, the animals are animals of any species or kind that are susceptible to or suffering from a disease or condition that causes sarcopenia or muscle atrophy, including animals of any age, species, health condition, and the like. In one embodiment, the animals are aging animals susceptible to or suffering from sarcopenia. In another embodiment, the animals are animals susceptible to or suffering from a disease or condition that causes muscle atrophy, e.g., cancer, AIDS, congestive heart disease, chronic obstructive pulmonary disease, renal failure, severe burns, and the like.

The isoflavones are any isoflavones known to skilled artisans. In various embodiments, the isoflavones are selected from the group consisting of isoflavones in the form of aglycons, glucosides, acetylglucosides, and malonylglucosides. Preferably the isoflavones are selected from the group consisting of biochanin A, daidzein, daidzin, glycitein, formononetin, equol, genistein, irilone, luteone, prunetin, pratensein, and glycitinn. In one embodiment, the isoflavones are soy isoflavones obtained from soy or administered to the animal by feeding soy or soy extracts to the animal. In another embodiment, the isoflavones are isoflavones substituted with one or more lignans or coumestans such as pinoresinol, lariciresinol, secoisolariciresinol, matairesinol, hydroxymatairesinol, syringaresinol, sesamin, enterodiol, enterolactone, and coumestrol.

The isoflavones are administered to the animals as required to function in the invention, e.g., preventing or treating sarcopenia or muscle atrophy. Administration amounts can easily be determined by skilled artisans, generally based upon the isoflavone(s) to be administered, the animal, the health conditions and status of the animal, the administration purpose, and the like. Preferably, the isoflavones are administered to the animals on a regular basis, preferably on a weekly basis, most preferably in a daily basis.

In various embodiments, the isoflavones are administered to the animals in amounts of from about 5 mg/day to about 5000 mg/day, preferably from 10 mg/day to about 2000 mg/day, more preferably from about 30 mg/day to about 500 mg/day, most preferably from about 50 mg/day to about 300 mg/day. In other embodiments, the isoflavones are administered to the animals in amounts of from about 0.001 to about 10 grams per kilogram of body weight per day (g/kg/day), preferably from about 0.05 to about 5 g/kg/day, most preferably from about 0.01 to about 1 g/kg/day. The isoflavones are administered for as long as there is a need for preventing or treating sarcopenia or muscle atrophy. For aging animals, isoflavone administration generally is needed for the remainder of the animal's life.

The isoflavones are administered to the animal in any suitable manner known to skilled artisans. Preferably, the isoflavones are administered to the animal in a composition containing isoflavones, preferably compositions intended for oral administration. In certain embodiments, the isoflavones are administered to the animal as a dietary supplement. In other embodiments, the isoflavones are administered to the animal in a food composition. In one embodiment, a food composition is formulated to provide "complete and balanced" nutrition for an animal, preferably a companion animal, according to standards established by the Association of American Feed Control Officials (AAFCO). In other embodiments, the food compositions are formulated as a companion animal food composition, including a dog or cat food composition. The dietary supplements or food compositions are formulated to contain one or more isoflavones in amounts sufficient to administer the desirable amounts of isoflavones to the animal, i.e., amounts of from about 5 mg to about 5000 mg or amounts sufficient to administer from about 0.001 to about 10 g/kg/day.

In various embodiments, the animal is a human. In others, the animal is a companion animal, preferably a dog or a cat.

In another aspect, the invention provides a package comprising one or more isoflavones and a label affixed to the package containing a word or words, picture, design, acronym, slogan, phrase, or other device, or combination thereof that indicates that the contents of the package contains isoflavones with beneficial properties relating to preventing or treating sarcopenia or muscle atrophy. Typically, such device comprises the words "prevents sarcopenia", "treats atrophy", "prevents or treats muscle wasting", or an equivalent expression printed on the package. Any package or packaging material suitable for containing the composition is useful in the invention, e.g., bag, box, bottle, can, pouch, and the like manufactured from paper, plastic, foil, metal, and the like. In a preferred embodiment, the package contains a food composition adapted for a particular animal such as a human, canine, or feline, as appropriate for the label, preferably a companion animal food composition for dogs or cats. In a preferred embodiment, the package is a can or pouch comprising a food composition useful for the invention.

In a further aspect, the invention provides a means for communicating information about or instructions for one or more of (1) using isoflavones for preventing or treating sarcopenia; (2) using isoflavones for preventing or treating muscle atrophy; (3) contact information for consumers to use if they have a question about the methods of the invention, e.g., about administering or using isoflavones for preventing or treating sarcopenia or muscle atrophy; and (4) nutritional information about isoflavones. Useful instructions include administration amounts and frequency for isoflavones. The communication means is useful for instructing on the benefits of using the invention and communicating the approved methods for administering the isoflavones to an animal. The means comprises one or more of a physical or electronic document, digital storage media, optical storage media, audio presentation, audiovisual display, or visual display containing the information or instructions. Preferably, the means is selected from the group consisting of a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, and any combination thereof.

In a further aspect, the invention provides for the use of one or more isoflavones to prepare a medicament. In another aspect, the invention provides for the use of isoflavones to prepare a medicament for one or more of preventing or treating sarcopenia or muscle atrophy. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

EXAMPLES

The invention can be further illustrated by the following examples, although it will be understood that these examples are included merely for purposes of illustration and are not intended to limit the scope of the invention unless otherwise specifically indicated.

Example 1

Thirty (30) lean Labrador Retrievers were fed food containing 25% more than their maintenance energy requirements (MERs) for nine (9) months. Fifteen (15) animals received a control food and fifteen (15) animals received the control food supplemented with isoflavones from 5% soy germ meal. Plasma samples were collected at baseline and every three (3) months during the trial. Nuclear Magnetic Resonance (NMR)-based metabolomics (or metabonomics) was used for the metabolic profiling of blood plasma to provide a comprehensive modeling of the metabolic changes in the animals. Standard proton NMR ($^1$H-NMR) spectroscopy of blood plasma samples are shown in FIG. 1. Such spectra exhibit a broad set of signals arising from proteins and lipoproteins together with many sharper peaks from major low molecular weight circulating metabolites, namely glucose, amino acids, and organic acids.

Figure 2:
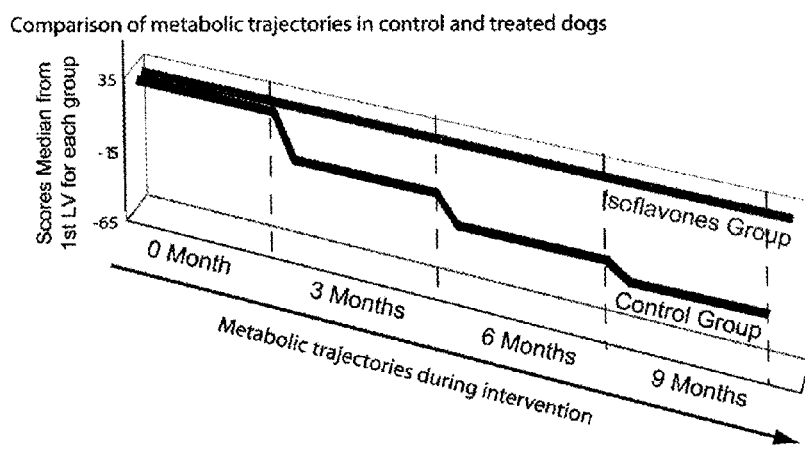
FIG. 2 illustrates a two-dimensional (2D) projection of the median of the scores obtained from the first latent variable for each group of animals at different periods.

The plasma $^1$H NMR spectra (i.e., the metabolite profiles) were processed with multivariate statistics to identify metabolic information (i.e., biomarkers) indicative of the physiological response of each animal to the isoflavones. Distinct metabolic trajectories were observed in animals that received isoflavones and control animals over time, as shown in FIG. 2. The data is shown in Table 1.

Referring to FIG. 2, the absence of metabolic variations over time in the animal group that received isoflavones is shown using a line starting from the same metabolic space as control animals (i.e., no metabolic differences at baseline) and remaining unchanged over time.

Referring to Table 1, the data show that an increase in muscle breakdown is prevented in animals that received the isoflavones. There was no increase in plasma circulating concentrations of leucine, valine, threonine, histidine, methionine, and 3-methyl-histidine. The results show that isoflavones are useful for preventing or treating muscle breakdown and wasting characteristic of sarcopenia and muscle atrophy caused by disease or other conditions. The $R^2X$ and $R^2Y$ values show how much of the variation in the data set X (NMR data) and Y (group assignment) is explained by the model, respectively. The $Q^2Y$ value represents the predictability of the model and relates to its statistical validity or robustness.

TABLE 1

Blood Plasma Metabolites Describing the Time-Related Changes in Control and Treated Dogs

| Metabolites Higher(H)/ Lower(L) Overtime When Compared to Baseline | Time 3 vs. 0 | | Time 6 vs. 0 | | Time 9 vs. 0 | |
|---|---|---|---|---|---|---|
| Groups | C | Iso | C | Iso | C | Iso |
| Model Descriptors CPMG Spectra | $R^2X =$ 0.20; $R^2Y =$ 0.97; | $R^2X =$ 0.30; $R^2Y =$ 0.92; | $R^2X =$ 0.23; $R^2Y =$ 0.97; | $R^2X =$ 0.27; $R^2Y =$ 0.91; | $R^2X =$ 0.25; $R^2Y =$ 0.97; | $R^2X =$ 0.31; $R^2Y =$ 0.92; |

TABLE 1-continued

Blood Plasma Metabolites Describing the Time-Related Changes in Control and Treated Dogs

| Metabolites Higher(H)/ Lower(L) Overtime When Compared to Baseline | Time 3 vs. 0 | | Time 6 vs. 0 | | Time 9 vs. 0 | |
|---|---|---|---|---|---|---|
| Groups | C | Iso | C | Iso | C | Iso |
|  | $Q^2Y = 0.32$ | $Q^2Y = 0.44$ | $Q^2Y = 0.33$ | $Q^2Y = 0.31$ | $Q^2Y = 0.63$ | $Q^2Y = 0.12$ |
| 3-D-Hydroxybutyrate |  |  | L (p = 0.0228) |  | L (p = 0.0301) |  |
| 3-methyl-histidine | H (p = 0.0058) |  | H (p = 0.0206) |  |  |  |
| Choline |  |  |  |  | L (p = 0.0318) |  |
| Glutamate | L (p = 0.0065) |  | L (p = 0.0036) |  | L (p = 0.0022) |  |
| Histidine | H (p = 0.0054) | L (p = 0.0426) | H (p = 0.0042) |  |  |  |
| Leucine |  | L (p = 0.0151) | H (p = 0.0164) | L (p = 0.0317) |  |  |
| Methionine |  |  | H (p = 0.0602) |  |  |  |
| Methyl Signal Of Fatty Acids | L (p = 0.0041) | L (p = 0.0000) | L (p = 0.0005) | L (p = 0.0000) | L (p = 0.0025) | L (p = 0.0001) |
| Threonine | H (p = 0.0050) | L (p = 0.0247) | H (p = 0.0002) | L (p = 0.0002) | H (p = 0.0253) |  |
| Valine | H (p = 0.0039) | L (p = 0.0097) | H (p = 0.0103) |  |  |  |
| Model Descriptors Diffusion-edited Spectra | $R^2X = 0.46$; $R^2Y = 0.81$; $Q^2Y = 0.18$ | $Q^2Y < 0$ * | $R^2X = 0.48$; $R^2Y = 0.81$; $Q^2Y = 0.33$ | $Q^2Y < 0$ * | $R^2X = 0.51$; $R^2Y = 0.89$; $Q^2Y = 0.61$ | $Q^2Y < 0$ * |
| Methyl Signal of Fatty Acids | L (p = 0.1304) |  | L (p = 0.0148) |  | L (p = 0.0030) |  |
| Proteins |  |  | L (p = 0.0104) |  | L (p = 0.0011) |  |
| Very Low Density Lipoprotein (VLDL) |  |  | H (p = 0.0070) |  | H (p = 0.0047) |  |

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims, the invention may be practiced otherwise than as specifically described.

What is claimed is:

1. A method for treating sarcopenia in an animal comprising administering to the animal an sarcopenia treating amount of equol or equol precursor, wherein the equol or equol precursor is administered to the animal in amounts of from about 0.05 to about 5 g/kg/day, wherein the animal is a dog or cat, wherein the equol precursor is an isoflavone that metabolizes to equol in a dog or cat.

2. The method of claim 1 further comprising administering one or more isoflavones, wherein the isoflavones are selected from the group consisting of isoflavones in the form of aglycons, glucosides, acetylglucosides, and malonylglucosides.

3. The method of claim 1 further comprising administering one or more isoflavones, wherein the isoflavones are selected from the group consisting of biochanin A, daidzein, daidzin, glycitein, formononetin, equol, genistein, irilone, luteone, prunetin, pratensein, and glycitinn.

4. The method of claim 1 wherein the equol or equol precursor is administered to the animal in amounts of from about 5 mg to about 5000 mg.

5. The method of claim 1 wherein equol or equol precursor is administered to the animal on a regular basis.

6. The method of claim 5 wherein the equol or equol precursor is administered to the animal in amounts of from about 0.01 to about 1 g/kg/day.

7. The method of claim 1 wherein the animal is an aging animal.

8. The method of claim 1 wherein the equol or equol precursor is administered as a dietary supplement.

9. The method of claim 1 wherein the equol or equol precursor is administered in a food composition.

10. The method of claim 9 wherein the food composition is formulated to provide complete and balanced nutrition for the animal.

11. The method of claim 10 wherein the animal is an aging animal.

12. The method of claim 1, wherein the equol or equol precursor is from soy isoflavones.

13. A method for treating muscle atrophy in an animal comprising administering to the animal a muscle atrophy treating amount of equol or equol precursor, wherein the equol or equol precursor is administered to the animal in amounts of from about 0.05 to about 5 g/kg/day, wherein the animal is a dog or cat wherein the equol precursor is an isoflavone that metabolizes to equol in a dog or cat.

14. The method of claim 13 further comprising administering one or more isoflavones, wherein the isoflavones are selected from the group consisting of isoflavones in the form of aglycons, glucosides, acetylglucosides, and malonylglucosides.

15. The method of claim 13 further comprising administering one or more isoflavones, wherein the isoflavones are selected from the group consisting of biochanin A, daidzein, daidzin, glycitein, formononetin, equol, genistein, irilone, luteone, prunetin, pratensein, and glycitinn.

16. The method of claim 13 wherein the equol or equol precursor is administered to the animal in amounts of from about 5 mg to about 5000 mg.

17. The method of claim 13 wherein the equol or equol precursor is administered to the animal on a regular basis.

18. The method of claim 17 wherein the equol or equol precursor is administered to the animal in amounts of from about 0.01 to about 1 g/kg/day.

19. The method of claim 13 wherein the equol or equol precursor is administered as a dietary supplement.

20. The method of claim 13 wherein the equol or equol precursor is administered in a food composition.

21. The method of claim 13, wherein the equol or equol precursor is from soy isoflavones.

* * * * *